United States Patent
Simons-Nikolova et al.

(10) Patent No.: US 10,424,409 B2
(45) Date of Patent: Sep. 24, 2019

(54) GUIDELINE-BASED PATIENT DISCHARGE PLANNING

(75) Inventors: Mariana Simons-Nikolova, Bolton, MA (US); Aleksandra Tesanovic, Eindhoven (NL); Rob Theodorus Udink, Lieshout (NL); Joseph E. Rock, Littleton, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 144 days.

(21) Appl. No.: 13/574,939

(22) PCT Filed: Feb. 4, 2011

(86) PCT No.: PCT/IB2011/050495
§ 371 (c)(1), (2), (4) Date: Jul. 24, 2012

(87) PCT Pub. No.: WO2011/095949
PCT Pub. Date: Aug. 11, 2011

(65) Prior Publication Data
US 2012/0296671 A1 Nov. 22, 2012

Related U.S. Application Data

(60) Provisional application No. 61/301,660, filed on Feb. 5, 2010.

(51) Int. Cl.
G16H 40/20 (2018.01)
G06F 19/00 (2018.01)
G16H 10/60 (2018.01)
G16H 50/30 (2018.01)
G16H 70/20 (2018.01)
G16H 70/60 (2018.01)

(52) U.S. Cl.
CPC .............. G16H 40/20 (2018.01); G16H 10/60 (2018.01); G16H 50/30 (2018.01); G16H 70/20 (2018.01); G16H 70/60 (2018.01); *G06F 19/325* (2013.01)

(58) Field of Classification Search
CPC ........ G06Q 50/22; G06Q 50/24; G16H 40/20; G16H 70/60; G16H 70/20; G16H 10/60; G16H 50/30; G06F 19/325
USPC ........................................................ 705/2, 3
See application file for complete search history.

(56) References Cited

U.S. PATENT DOCUMENTS

| | | | |
|---|---|---|---|
| 8,052,611 B2* | 11/2011 | Wariar | A61B 5/0031 600/508 |
| 2005/0192848 A1* | 9/2005 | Kozminski et al. | 705/3 |
| 2007/0129612 A1* | 6/2007 | Ten Eyck et al. | 600/301 |

(Continued)

OTHER PUBLICATIONS

EPO: Notice From the European Patent Office Concerning Business Methods, Oct. 1, 2007.

*Primary Examiner* — Elaine Gort
*Assistant Examiner* — Amanda R. Covington

(57) ABSTRACT

A system and method for guideline-based discharge planning of a patient from a facility, comprising determining via a processor whether a patient meets predetermined discharge criteria from the facility, generating a first signal indicative of the patient's risk of re-admission to the facility, generating a second signal indicative of a plan for providing care for the patient, generating a third signal indicative of a status of the patient for a post-discharge care report, and generating a fourth signal indicative of instructions to discharge the patient from the facility.

20 Claims, 9 Drawing Sheets

(56) References Cited

U.S. PATENT DOCUMENTS

| | | | |
|---|---|---|---|
| 2008/0009686 A1* | 1/2008 | Hendrich | 600/301 |
| 2008/0033760 A1* | 2/2008 | Osgood | G06Q 10/06 |
| | | | 705/3 |
| 2008/0228090 A1* | 9/2008 | Wariar et al. | 600/508 |
| 2010/0057490 A1* | 3/2010 | Kocis et al. | 705/2 |
| 2011/0087501 A1* | 4/2011 | Severin | 705/3 |
| 2011/0212855 A1* | 9/2011 | Rafnar et al. | 506/9 |

* cited by examiner

GUIDELINE-BASED PATIENT DISCHARGE PLANNING

FIELD OF THE INVENTION

The following relates to patient discharge planning.

BACKGROUND OF THE INVENTION

Clinical decision support systems utilizing Clinical Decision Support (CDS) tools have become a leading response to the growing demand for the promotion of standards-based care delivery. CDS tools are important components of clinical Information Technology (IT) systems and may directly improve patient care outcomes and the performance of healthcare organizations. The development and use of CDS tools at the point of care offers medical professionals the ability to analyze and work with patient data in real-time while making critical decisions.

With respect to the cost of treatment and complexity of management of patients in a medical facility, in particular heart failure (HF) patients because of the difficult HF etiology and many co-morbidities like sleep apnea, hypertension, diabetes, chronic obstructive pulmonary disease (COPD), and renal dysfunction, the demand is huge and growing because of an aging population and in part to re-hospitalization of the HF patient after discharge. A large part of this cost, estimated to be at forty-two (42%), is regarded as preventable by proper treatment prior to and after discharge from the hospital.

Nowadays discharge criteria are physician dependent, i.e., they differ per country, hospital, and even physician. The American College of Cardiology/American Heart Association (ACC/AHA) and the European Society of Cardiology (ESC) guidelines do not specify discharge criteria. Only the Heart Failure Society of America (HFSA) guidelines list a number of discharge criteria with Strength of Evidence C (=low) indicative of missing evidence on how effective those discharge criteria are with respect to outcomes. Further, current methods of determining whether HF patients are at a high risk of adverse effects (e.g., HF exacerbation often result in frequent re-admissions and high mortality rates) are used only in clinical research and not in daily practice due to missing tools, bringing the complex risk nomograms into the daily clinicians workflow. The existing methods for medical professionals to prepare the patient for disease management in out-of-hospital settings and propose guideline-based post-discharge therapy can be improved with respect to efficiency and effectiveness. Current methods of providing discharge instructions for HF patients include approximately one hour of manual instruction by the care provider on the last day of the hospital stay which leads to patient information overload and poor post-discharge care results.

In addition, there is currently no method of effectively ensuring continuity of care from the hospital care team who treated the HF patient by sharing the status of the HF patient with other professionals responsible for post-discharge care of the HF patient.

SUMMARY OF THE INVENTION

Aspects of the application address the above matters, and others.

According to an aspect of the invention, a method comprising determining via a processor whether a patient meets predetermined discharge criteria from a facility, generating a first signal indicative of the patient's risk of re-admission to the facility, generating a second signal indicative of a plan for providing care for the patient, generating a third signal indicative of a status of the patient for a post-discharge care report, and generating a fourth signal indicative of instructions to discharge the patient from the facility.

According to another aspect of the invention, a method comprising determining via a processor a quantity of patients in first, second, third and fourth groups, the first group including patients that have been discharged with discharge criteria being met, the second group including patients that have not been discharged with the discharge criteria not being met, the third group including patients that have been discharged without the discharge criteria being met, and the fourth group including patients that have not been discharged with the discharge criteria being met; generating and sending a care provider an electronic notification when a patient is classified in either of the third or fourth groups; updating the discharge criteria based on an analysis of the first and second groups for further defining patients to be classified in the first and second groups; and deriving new discharge criteria based on analysis of the third and fourth group to minimize the number of recently discharged patients in the third and fourth groups.

According to another aspect of the invention, a method comprising generating via a processor a signal indicative of a status of a patient for a post-discharge care report tailored to at least one post-discharge care provider from a care team at a medical facility, the report comprising: a first section which includes a patient's data for all post-discharge care providers and for the patient; and a second section which includes the patient's information tailored for the at least one care provider (group 1 of users) and the patient and his family (group 2 of users). Tailoring refers to levels of explanation and details of information that differs for the two groups aforementioned.

According to another aspect of the invention, a method comprising generating via a processor a first signal indicative of a risk of a patient's re-admission to a facility during a predetermined post-discharge period, generating a second signal indicative of contributing factors to the risk, and generating a third signal indicative of a care plan to reduce the risk.

According to another aspect of the invention, a method comprising generating via a processor a first signal indicative of a care plan for a HF patient with a medical condition based on at least one first predetermined care guidelines, generating a second signal indicative of conflicts between multiple additional predetermined care guidelines and the at least one first care predetermined care guidelines the care plan is based on for the HF patient with co-morbidity, and generating a third signal indicative of contraindications of not following the at least one first predetermined care guidelines based in the care plan.

The aspects defined above and further aspects of the invention are apparent from the examples to be described hereinafter and are explained with reference to the examples.

The invention will be described in more detail hereinafter with reference to examples but to which the invention is not limited.

FIG. 1 illustrates a block diagram of asystem for guideline-based patient discharge planning;

FIG. 2 illustrates a flow diagram of a method for guideline-based patient discharge planning;

FIG. 3 illustrates a block diagram of patient grouping according to the percentage of patients who have or have not been discharged according to whether the patients have met or not met discharge criterion;

FIG. 4 illustrates a block diagram of patient grouping for a particular cardiology department according to the percentage of patients who have or have not been discharged according to whether the patients have met or not met the particular cardiology department's discharge criterion;

FIG. 5 illustrates a graphical user interface authoring tool for customization of default discharge criteria for patients;

FIG. 6 illustrates a table of relations between patient discharge groups and clinical outcomes of 30-days post-discharge re-admission rate;

FIG. 7 illustrates a screen shot of a patient risk stratification module;

FIG. 8 illustrates a graphical user interface authoring tool for an in-hospital personal care plan (PCP) for a patient starting with the PCP design steps;

FIG. 9 illustrates a zoom out of the graphical user interface authoring tool of FIG. 8 of the patient's pathway in the PCP and the content mapping in the PCP;

FIG. 10 illustrates a zoom out of a timeline representation of a patient pathway during the PCP of FIG. 9 illustrating the blocks in the pathway which have been completed, the patient's score on an assessment, and an alert in case of a low score;

FIG. 11 illustrates a graphical user interface authoring tool for generating a tailored summary discharge report for a patient;

FIG. 12 illustrates a graphical user interface authoring tool for configuring actor profiles and level of interest;

FIG. 13 illustrates a graphical user interface authoring tool for configuring actor profiles and level of interest; and FIG. 14 illustrates a graphical user interface for presenting risk stratification, including the degree of risk and the influence of a support service on the degree of risk.

Figure 1:
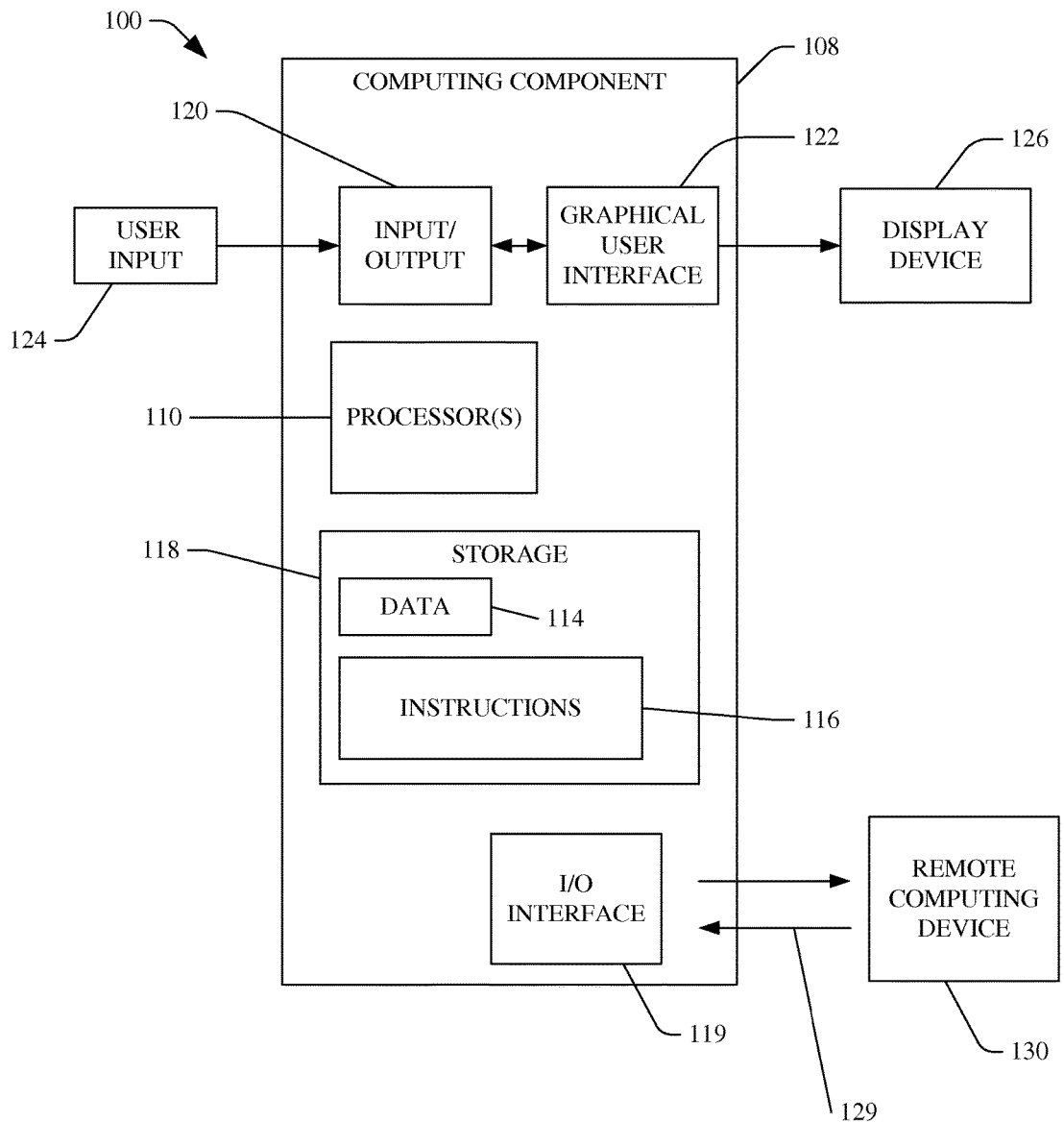
FIG. 1 illustrates an exemplary system 100 for guideline-based discharge planning of a patient receiving treatment at a medical facility. The patient is for example a heart failure (HF) patient and the medical facility may include a hospital having a cardiac unit. However, the patient may be any other type of patient receiving treatment at any type of facility since the present example is only presented for demonstration purposes and is not intended to be limiting.

The system 100 includes for example a computing system 108 such as a workstation, a desktop computer, a laptop, a handheld computing device, a communication device or the like. The computing component 108 includes one or more processors 110 and storage 118 such as non-transitory computer-readable medium encoded with data 114 and/or instructions 116 which, when executed by the processor 110, cause a computing system 108 to perform various acts. The illustrated storage 114 is encoded at least with instructions 116 for guideline-based discharge planning.

Input/output 120 provides an interface for receiving input from a user input 124 such as algorithm parameters and patient information and/or conveying information via a graphical user interface (GUI) 122 including the graphical user interface tools described below to a user of the system 100 via a display device 126. The computing system 108 may include an I/O interface 119 for connecting computing system 108 to a remote computing device 130 having databases containing data including but not limited to patient data and guidelines for guideline-based planning of patient care that may be retrieved by one or more processors 110 and stored in storage 118. The I/O interface 119 of computing system 108 may connect computing system 108 to the remote computing device 130 via a communications link 129. The I/O interface 119 includes but is not limited to a network interface, modem or other communications device. The communications link 129 includes but is not limited to a computer network such as the world wide web, an intranet, or a telephone network.

The system 100 performs a discharge criteria check of a patient admitted to a hospital for treatment; generates patient risk stratification; generates a personalized care plan (PCP) that aids medical professionals in choosing the best discharge instruction plan based on guidelines and current patient status; generates a summary discharge report tailored to at least one post-discharge care provider from a multi-disciplinary team of care providers providing treatment at the hospital, and/or other algorithms. The algorithms may also include CDS tools as is known to one of ordinary skill in the art.

Figure 2:
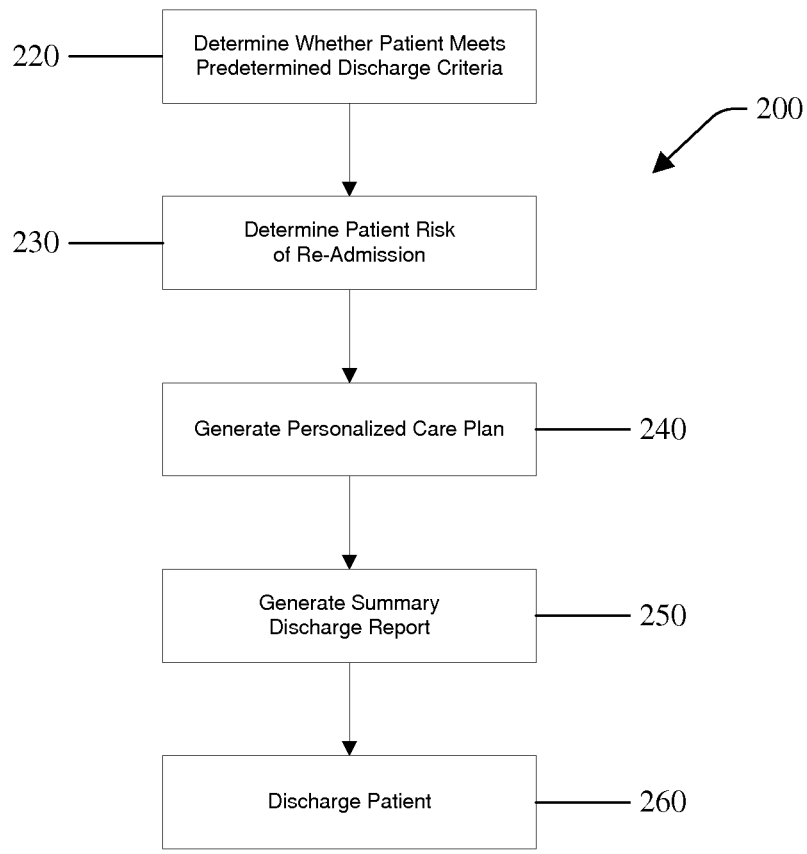

With reference to FIG. 2, illustrated is another example method 200 for guideline-based discharge planning of a patient admitted to a hospital for treatment for implementation on the system 100 of FIG. 1. The method 200 is described in connection with a heart failure (HF) patient and is performed after the patient has been treated for a medical condition and is stabilized.

It should be appreciated that the ordering of the acts is not limiting. As such, one or more of the acts may occur in a different order, including concurrently with one or more other acts. In addition, one or more of the acts can be omitted and/or one or more other acts can be added.

At 220, it is determined whether the patient meets predetermined discharge criteria;

At 230, the patient's risk stratification is determined;

At 240, a personal care plan (PCP) is generated for the patient;

At 250, a summary discharge report is generated for the patient; and

At 260, instructions for discharging the patient from the hospital are generated.

With respect to act 220 of the method 200 of FIG. 2, the discharge criteria are determined by one or more of the following exemplary and/or alternative means described below.

Figure 3:
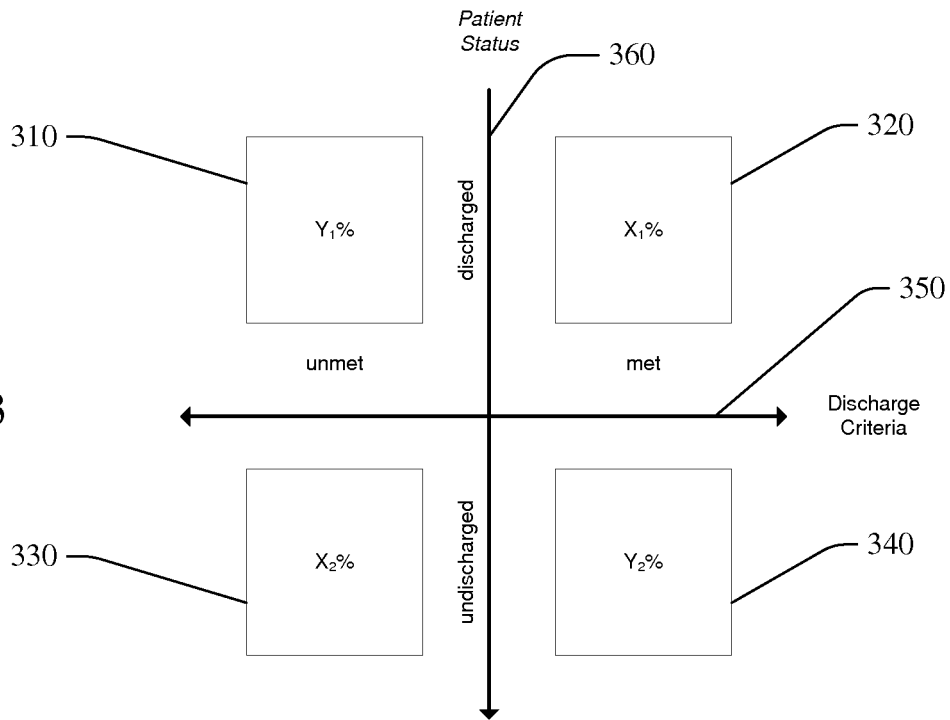

As one non-limiting example, the method 200 employs a self-learning algorithm for identifying discharge criteria or rules based on historical data and/or evidence from patients risk strategy nomograms (graphic representation of numerical relationships). FIG. 3 illustrates an approach for identifying discharge criteria based on historical data to: quantify patients in $X_{1,2}$ and $Y_{1,2}$ groups; alert the healthcare provider if a patient belongs to either $Y_1$ or $Y_2$ groups; extend a set of existing discharge criteria based on analysis of X groups (special interest to new objective criteria health care professionals may use to classify a patient in groups $X_1$ and $X_2$), derive new discharge criteria based on analysis of Y groups (special interest to subjective criteria medical professionals may use to classify a patient in groups $Y_1$ and $Y_2$); and minimize $Y=Y_1+Y_2$ ultimately close to 0%.

Note that $X_1$ and $X_2$ groups 320, 330 consists of discharged patients that were discharged with the discharge criteria being met and undischarged patients with the discharge criteria not being met, respectively. $Y_1$ and $Y_2$ groups 310, 340 consists of patients being discharged with the discharge criteria not being met and patients that were discharged with the discharge criteria being met, respectively. These groups can be problematic due to high re-admissions and long length of hospital stay, respectively. In FIG. 3, the patient status, e.g. discharged and undischarged, is shown along the axis 360 while the discharge criteria, e.g., unmet and met, are shown along the axis 350.

In another non-limiting example, the method 200 uses an algorithm that includes using evidence from patient risk strategy nomograms (see FIG. 7), e.g., a set of discharge criteria for patients at high risk of 30 days post discharge re-admission or mortality.

Figure 7:
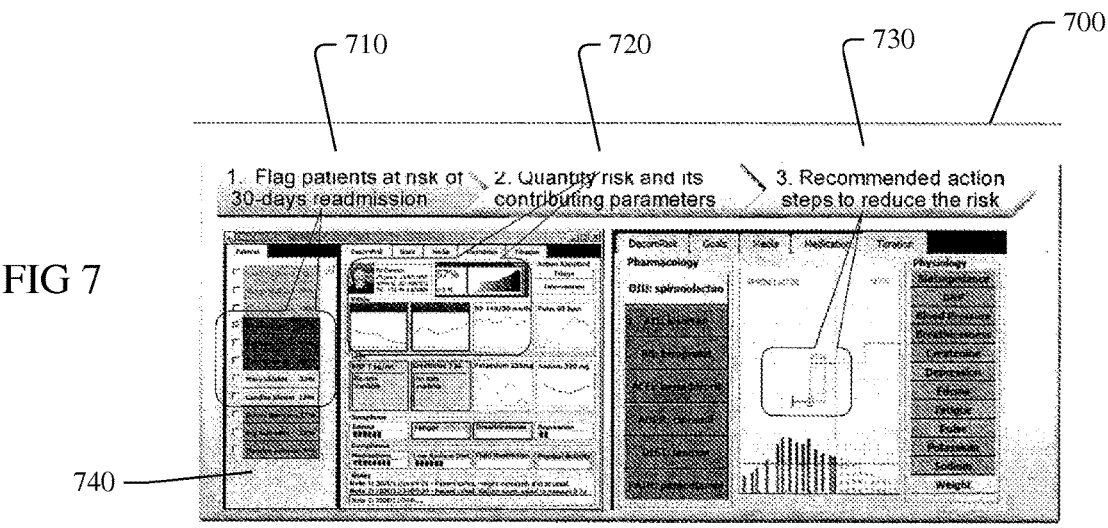

In another non-limiting example, the method 200 presents a graphical user interface representation of discharge criteria and the patient status with respect to these criteria, including overlaying health parameters. If discharge criteria are not satisfied, a list of actions necessary to meet these criteria will be provided. Each action is accomplished with an action plan (integrated with hospital resource planning), and cost estimate in terms of resources spent versus desired outcome (e.g., nurse hours versus reduced risk of re-hospitalization. This action plan is illustrated in FIG. 7, block 730.

In another non-limiting example, the method 200 includes using visualization of statistical relations between patients discharged groups (X or Y) and outcomes. The latter may be clinical (re-admission rate, length of hospital stay, ED visits, mortality), hospital (cost savings, workflow optimization, quality of care), or patients outcomes (quality of life, satisfaction with treatment). CDS authoring tools for medical professionals to update their discharge procedures based on the relations identified are contemplated.

Figures 5, 6:
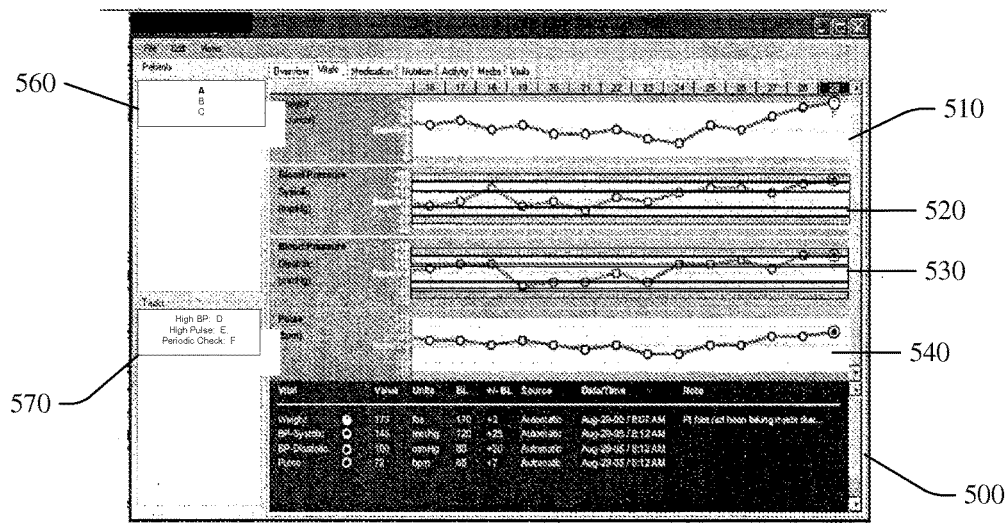

The table 600 shown in FIG. 6 illustrates a way to visualize the relations between the $X_1$ and $Y_1$ discharge groups illustrated in FIG. 3 and a clinical outcome such as re-admission rate (illustrated in columns 635 and 645, respectively). In this example, the clinical outcome 30-days post-discharge re-admission rate is selected for the year 2010 for the months of January through December (column 610), similar illustrations may be provided for all other outcomes discussed above. The totals of the outcomes of the patient discharge groups $X_1$ (630) and $Y_1$ (640) are shown in column 620 for the year 2010 for the months of January through December. The table 600 in FIG. 6 illustrates that most of the patients who were re-admitted within the 30-days post-discharge period are from the $Y_1$ group 640, i.e., they were discharged prior to re-admission with unmet discharge criteria.

As one example, the discharge criteria or rules above include multiple parts, including a condition and a discharge decision. A condition is a boolean expression evaluated with patient's data such as lab tests, electrocardiogram (ECG), echo, vitals, fluid volume overload, knowledge, compliance, etc., in order to check whether a given discharge criterion is satisfied or not. Examples of discharge decision includes "Patient A: Ready for discharge" or "Patient B: Not ready for discharge" and/or other parts.

Figure 4:
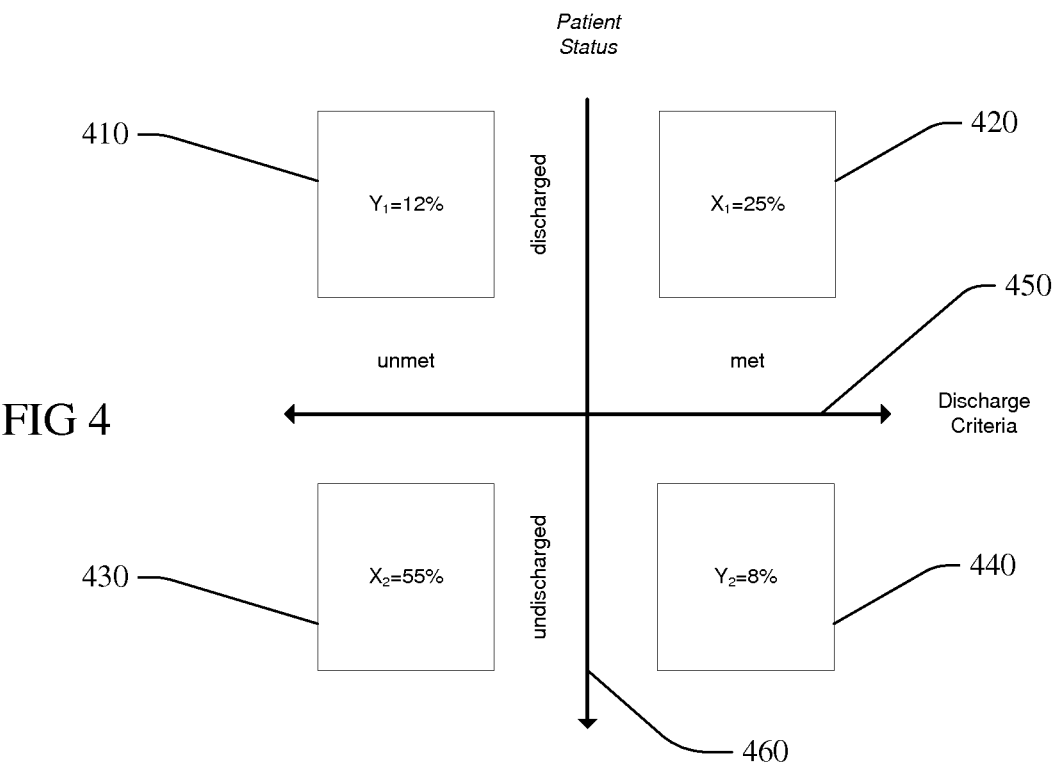

A set of discharge criteria or rules form the core of the discharge criteria check system 100. First, the system 100 can perform an automated discharge criteria check. Second, the system 100 can quantify the $X_{1,2}$ and $Y_{1,2}$ groups of patients for a particular cardiology department as illustrated in FIG. 4. Note that in FIG. 4 the $X_1$ and $X_2$ groups 420, 430 consist of discharged patients that were discharged with the discharge criteria being met and undischarged patients with the discharge criteria not being met, respectively, for the subject cardiology department. $Y_1$ and $Y_2$ groups 410, 440 consist of patients due to re-admissions and long length of hospital stay with the patients being discharged with the discharge criteria not being met and patients that were undischarged with the discharge criteria being met, respectively, for the subject cardiology department. In FIG. 4, the patient status, e.g. discharged and undischarged, is shown along the axis 460 while the discharge criteria, e.g., unmet and met, are shown along the axis 450. For example, in FIG. 4, $X_1$=25%, $X_2$=55%, $Y_1$=12%, and $Y_2$=8%.

The quantification is based on comparison between the algorithm output and historical data taken from patient files (e.g., documented decisions of cardiologists and discharge planning nurses). High percentages in $Y_{1,2}$ groups are indicators of high cost patients due to frequent re-admissions ($Y_1$) and long length of stay ($Y_2$). Therefore, costs optimizations could be achieved by minimizing $Y_{1,2}$. This could lead to discovering new discharge rules and/or new propositions as discussed in the examples below.

For example, a first patient A (FIG. 5, block 560) belongs to group $Y_1$, i.e., the discharge criteria check system 100 classified patient A as "Not ready to discharge," however, patient A has already been discharged by the cardiologist. There are two options, the decision to discharge the patient by the cardiologist may invoke a reccomendation to be reversed by the system 100 or be a conscious choice triggered by a rational like: "BP systolic is not fully stabilized, however, the patient will be closely monitored at home via a remote patient management (RPM) system." If this rational has been applied to many patients and has statistical relevance, the system 100 may propose it as a new discharge criteria rule. In particular, it's a refinement of an existing rule with respect to BP replacing the concepts of measurements within-the-boundary and out-of-boundary with measurements within predetermined zones in a graphical user interface authoring tool displayed on display device 120. This is illustrated in FIG. 5 for the systolic and diastolic blood pressure measurements in blocks 520, 530, respectively.

In another example, a second patient B belongs to group $Y_2$, i.e., the discharge criteria system 100 classified patient B as "Ready to discharge," however, patient B has not been discharged by the cardiologist. There are two options: the decision by the cardiologist may invoke a reccomendation to be reversed by the system 100 or be a conscious decision triggered by a rational like: "The patient is without social support at home and it's Friday, let's monitor patient B in the hospital another 3 days and discharge patient B on Monday." This rational protects the patient's health; however, it also may lead to increased length of hospital stay, which is costly. The rational could lead to a new discharge rule like "The patient without social support at home can be discharged on Friday under increased surveillance of a medical call center in the weekend and an RPM service".

In another non-limiting example, the method 200 uses a graphical user interface authoring tool 500 for customization of default discharge criteria per hospital and per patient. The graphical user interface authoring tool 500 would have the capability to enable authorized medical professional to modify, add, and remove discharge criteria important to a particular hospital department and in particular to a specific patient. The graphical user interface authoring tool 500 is illustrated in FIG. 5.

The discharge criteria may differ from a country to country, from hospital to hospital and even from a treating physician to the another. However, there are commonalities in discharge criteria; for example, each patient needs to be stabilized with respect to renal function, blood pressure (illustrated in FIG. 5, blocks 520, 530) and weight (illustrated in FIG. 5, block 510), meaning that the patient's measurements should be within defined boundaries. This is an example of a commonality across hospitals and patients. The customization per hospital and patient takes place, for example, in defining the baseline and the boundaries of the aforementioned predetermined zones, which are patient specific. Hence, the medical professionals and hospital would ideally like to have their (tailored) discharge criteria, while not spending significant effort in the tailoring process. Thus, the graphical user interface authoring tools are contemplated that would present to medical professionals common "default" criteria known as variations, in a graphical format easily recognizable and usable by that medical professional.

The graphical user interface authoring tools enable medical professionals to easily select the discharge criteria that are applicable for their current practice, e.g., by "drag & drop" techniques in an editing area. Moreover, the graphical user interface authoring tools would perform the discharge criteria cross-checking and notify the user in case of incompatibility. Further, the personalization per patient may be done either manually or via a smart self-learning algorithm that would take as an input patient medical history and current health status, and suggest as an output patient specific measurement baseline and boundaries. The CDS authoring tools are applicable for all diseases that require extensive discharge criteria; they are not limited to HF.

In another non-limiting example, the method 200 uses a discharge criteria domain model and a set of transitions and modelling rules that enable formalization and customization of discharge criteria per hospital and per patient. The discharge criteria and protocols differ per hospital and therefore, the discharge criteria CDS tool needs to be flexible to support this diversity. It will do so by separating the models that describe the discharge criteria and protocols from the engine executing these models. Then, hospitals may make their own model aligned with their own protocols, which will be an input to the system 100. The later will use generic technology independent of the hospital specific model.

In another non-limiting example, the method 200 involves a technique for collecting/validating a statistically relevant set of discharge criteria (e.g., via a series of face-to-face meetings and on-line surveys) from multiple sites and medical professionals. If systems similar to system 100 in different hospitals are connected, effectiveness and efficiency of the discharge criteria models described above, and especially part of these models, may be compared online and offline. This comparison may be used to generate recommendations for models improvement.

For example, hospitals A and B have both developed their own model for discharge criteria and use it in their daily operation. By relating these discharge models to clinical outcomes as illustrated in the table 600 of FIG. 6 described above the system 100 may show evidence that, for example, the model of hospital A leads to better clinical outcomes for a specific sub-population (e.g., illiterate HF males with diabetes) than the model of hospital B. The system 100 may come up with different levels of recommendations (also depending on the proprietary nature of the hospitals protocols), for example: for sub-population X, other hospitals have . . . % better outcomes on . . . ," and for sub-population X, other hospital . . . has . . . % better outcomes on . . . , by using protocol . . . ".

In another non-limiting example, the method 200 uses a technique for evaluating the behaviour/pattern of a patient's measured values as an additional criterion in the discharge process. Data on a low-variability glide slope into normal range predicts better post-discharge performance than a patient with high-variability in measurements over time who may still meet the criteria.

For example, a patient with weight (illustrated in FIG. 5, block 510) within-the-boundary at the 6th day of hospitalization, i.e., the discharge criterion with respect to weight is satisfied if it's based on a single point of measurement. However, the discharge criteria could take into account multiple measurement points (i.e., rather a trend than a single measurement point) and the behavior pattern of patient's weight during at least 6 days of hospital stay. The latter may have either low or high variability glide slope into normal range. An example of low variability is a weight that quickly decreases after diuretics treatment started at the first day of hospitalization and in the last couple of days smoothly approaches the baseline value following a normal medication regime. This weight behavior pattern could be indicative for stable post-discharge performance and therefore readiness for discharge. An example of high variability is a weight that has been fluctuating a lot in the past 6 days and several changes in the medication regime were necessary. This weight behavior pattern could be indicative for unstable post-discharge performance and necessity for either longer hospital stay or increased surveillance during the post-discharge period.

In another non-limiting example, the method 200 includes employing a technique for incorporating prior (home or prior hospitalization) patient information, e.g., blood pressure, pulse, weight (illustrated in FIG. 5, blocks 510, 520, 530 and 540, respectively), etc., into the discharge decision of a patient in the current episode.

While most discharge criteria are based on the data gathered during the stay of the patient in the hospital, other data from other systems may be incorporated. This may include data gathered via Remote Patient Monitoring systems, e.g., but also from public health records located in, for example, a remote computing device such as the remote computing device 130 illustrated in FIG. 1. This may be data gathered in the context of either HF or co-morbidity (like diabetes, COPD, etc) or preventive check-up or any other reason. On one hand, this data may be used to get additional information on how the patient behaves before hospitalized and may predict possible complications during the post-discharge period. On the other hand, this data may be used as additional measurement points for the discharge criteria as elaborated in the previous examples.

For example, a non-compliant patient as determined by daily measurement via a RPM system has a higher risk of complication during the post-discharge period and it might be necessary to get additional education before discharge, and/or take care that the patient is really stable at the point of discharge. For a compliant patient that has been very conscious with respect to measuring their vitals before hospitalization it might be satisfactory to discharge the patient earlier if proper escalation measurements are in place to handle worsening.

This information could be incorporated into the discharge criteria list by a category, "pre-hospital patient behavior," the system could propose additional actions to be taken before discharge additional discharge criteria for that patient, e.g., extra education on self-monitoring.

With respect to act 230 of FIG. 2, the method 200 determines the patient's risk stratification (e.g., the risk (expressed as a percentage) that the patient has of post-discharge re-hospitalization or mortality).

The method 200 can provide a visual presentation of the patient risk stratification rules in a risk stratification module and automated generation of an actionable plan (illustrated in FIG. 7) for the hospital care team that includes: an alert specifying the patient's risk of re-hospitalization during the 30 day post-discharge period (illustrated in FIG. 7, block 710); in addition a risk score (quantifying the risk) and confidence level (illustrated in FIG. 7, block 720) will be presented to the medical professionals; proper visualization and quantification of contributing parameters to the risk (illustrated in FIG. 7, block 720); and recommended action steps to reduce the risk (illustrated in FIG. 7, block 730), e.g., use of a patient specific out-of-hospital care plan provided via a telehealth service during the post-discharge period. The out-of-hospital care plan covers pharmacological as well as non-pharmacological treatment and counseling and follow-up visits. The method 200 may suggest which modules of the care plan may reduce the high risk of a specific patient.

The method 200 may guide the medical professionals' attention to patients that have a high(er) risk of adverse events, e.g., post-discharge re-hospitalization and/or mortality. This could for example be done either by sending alerts to the medical professional (via e-mail, sms, or other means); showing a (ordered) list of these patients to the medical professional (FIG. 7, block 740); highlighting these patients in the patient list (with special colors, . . . ) (FIG. 7, block 740); or by adding flag icons to the patient in a patient list or when representing the patient data (FIG. 7, block 740). When viewing the patient data or the electronic discharge form, the system may quantify the re-hospitalization risk. This could be a number indicating a percentage, some low-med-high indication and/or color coding (FIG. 7, blocks 720 and 740). Since often these calculations are based on historical evidence and statistical data and probabilities, also a confidence level can be represented indicating how confident the system 100 is that the number is correct.

For example, in case there are several randomized clinical trials providing evidence then the confidence level is high. However, if a single observational study is available the confidence level is low.

Since not only the risk of re-hospitalization is important for further handling of the patient, the underlying parameters on which that conclusion is build must be considered. Therefore, these contributing parameters (FIG. 7, block 740) are also indicated to the care professional, e.g., via highlighting them in a total patient overview.

When the risk and the underlying aspects are known and understood, the method 200 may generate an action plan(s) on how the patient should be treated. This could include additional diagnoses, pharmacological treatment, non-pharmacological treatment, etc. The method 200 may present these options to the medical professional in such a way that the medical professional may easily select the best (according to guidelines, historical evidence, etc.) treatment option, but may also select other treatment options in case the medical professional has other insights on how the patient should be treated.

As another option, act 230 of method 200 can be based on knowledge discovery techniques for identifying cut-off values of (combinations of) existing parameters related to high risk of re-admission or new parameters contributing to the multi-parameter algorithms for patient risk stratification.

Calculating the risk or re-admission for a specific patient can be done in different ways, e.g., based on public or proprietary nomograms provided by third parties, often based on specific clinical trials. It may also be done based on (online/offline, real-time/episodic) analyses of the historical data of the hospital itself. From these analyses the system may formulate hypotheses of cut-off values of existing or new parameters.

The outcome of the analyses may be used in different ways: it can be tested and validated separately in clinical trials and only after it has been proven incorporated into the system 100 as an improved risk calculation scheme; the system 100 may use those hypotheses on top of validated risk calculation algorithm indicating a low confidence level of the hypotheses; or system 100 may present it as annotations in the risk analyses results, e.g., it uses a validated risk calculation algorithms and shows its conclusions. However, when it appears that a rule does not (or only partially) holds from analyses of it's own patient data an indication is provided to the medical professional with a comment like "this rule partly conforms to the historical data in this hospital."

As a further option, the act 230 of method 200 can use CDS tools for linking the clinical parameters contributing to the risk of a patient to the post-discharge care, e.g., a tool that links the clinical criteria of a patient with summary discharge reporting to highlight which clinical parameters are of interest for which medical professional who are following the patient after discharge.

When non-compliance to self-reporting of symptoms was identified as an important aspect contributing to the risk for re-hospitalization, the method 200 adds a specific recommendation to the nurse in the clinic as well as the home care nurse to pay additional attention to symptoms reporting. For example, when high salt-intake was a main contributing aspect, an additional note could be incorporated in the discharge report to the dietician.

With respect to act 240 of FIG. 2, the method 200 generates a personal care plan (PCP) for the patient to prepare the patient for disease management in out-of-hospital settings and propose guideline-based post-discharge therapy.

As yet another option, the method 200 includes handling conflicting guidelines recommendations, especially when the patient suffers from many co-morbidities. This includes visualizing the conflict between the guidelines for the patient in a specific situation, and the consequences of not following the guidelines.

For example, a HF patient with strict fluid restrictions that has been hospitalized with STEMI (ST Elevated Myocardial Infarction). The standard guidelines for the treatment of STEMI are likely contraindicative for this particular patient. The system 100 will identify which steps in both the PCP and the guideline(s) are at odds with each other and will offer personalized recommendations that aid the clinician in weighing the contraindications as prescribed by the multiple guidelines.

Additionally, the method 200 uses tools to aid the medical professional in choosing the best discharge strategy for medication therapy based on guidelines and more specifically current patient status. These tools would bring medical algorithms (e.g., in-hospital up-titration and diuretic dose management) into PCP and would tailor the medication therapy toward the patient (also given the co-morbidities).

Each time a patient is discharged, the medical professional needs to ensure that the patient is stable (e.g., the patient has appropriate diuretics quantity or beta-blockers (BB), patients with HF with LVSD (left ventricular systolic dysfunction) and without angiotensin-converting enzyme inhibitors (ACEi) contraindications are prescribed an ACEi, etc.), and that this therapy is in line with the co-morbidities that the patient has. The tool may offer medical professionals recommendations for each patient with respect to medications, e.g., decrease/increase dose of ACEi before discharge, labs to be re-checked, e.g., schedule labs to ensure that BB titration can be done safely after discharge, and also co-morbidities, e.g., patient is known to have COPD, and ensuring that the patient is instructed on differences between COPD and HF worsening detection.

Furthermore, the method 200 employs CDS tools that may, based on the risk factors, discharge criteria, and current medication therapy, suggest the most appropriate (additional) education content for the patient.

Normally, an educational program for (pre and post-discharge) the patient is created based on: the specific medical condition (such as HF) patient pathway in hospital; and the topics that are relevant for that pathway given specific patient health-condition. This means that education is tailored toward the patient's needs. However, in some cases, e.g., the patient gaining weight and refusing to increase diuretics dose, the medical professionals would like to provide appropriate tutoring for the patient that is directly related to the intervention that is being suggested. This tutoring is additional to the educational program of the patient as it is situation and intervention dependent. The contemplated tool may assist medical professionals in providing intervention-related tutoring while saving time and effort.

For example, when the patient's weight increases and the medical professional decides to introduce additional diuretics to the patient's medication regime, the system 100 may automatically suggest (directly to the patient via bed-side TV or after approval by the medical professional) the "diuretics change interventional educational program". For this patient the method 200 will take into account the known history of medication non-compliance, e.g., refusing to take increased diuretics dose; known history of salt restrictions non-compliance, e.g., eating too many herrings; and results of a dynamic assessment of comprehension and retention of education over diuretics. The system 100 can subsequently suggest remedying the above situations by offering additional items to the personal care plan such as, e.g., a teaching quiz on the relation of diuretics and weight; skill building tips on a low sodium diet, e.g., a pre-composed menu; and an animated picture-based tutorial on the importance of using diuretics.

In another non-limiting instance, the method 200 invokes a graphical user interface authoring tool 800 (FIG. 8) for in-hospital personalized care plans (PCP) covering discharge instructions on a primary disease (e.g. HF) and co-morbidities (diabetes, COPD, sleep apnea, etc.)

The PCP authoring tool 800 will support medical professionals in clinical decisions they are faced with in developing hospital specific PCP covering all steps of patients in-hospital care—from point-of-admission to point-of-discharge and beyond, i.e., point-of-transition to out-patient settings. The PCP authoring tool 800 aids medical professionals in creating automated and interactive patient pathways with: structure based on international and local clinical guidelines and professional medical judgment covering primary disease and co-morbidities; and with the possibility to specify the type of elements in the pathways structure (defined in the first step), e.g., an interactive assessment, an educational feedback, a skill building tip, etc.; and the possibility of choosing from a library of content elements linked to the type of elements specified in the second step above.

The PCP authoring tool 800 will also support medical professionals in clinical decisions they are faced with in the management phase of PCP, among others assigning a PCP to specific patient, personalizing, migrating, suspending and modifying it during its execution.

Figure 8:
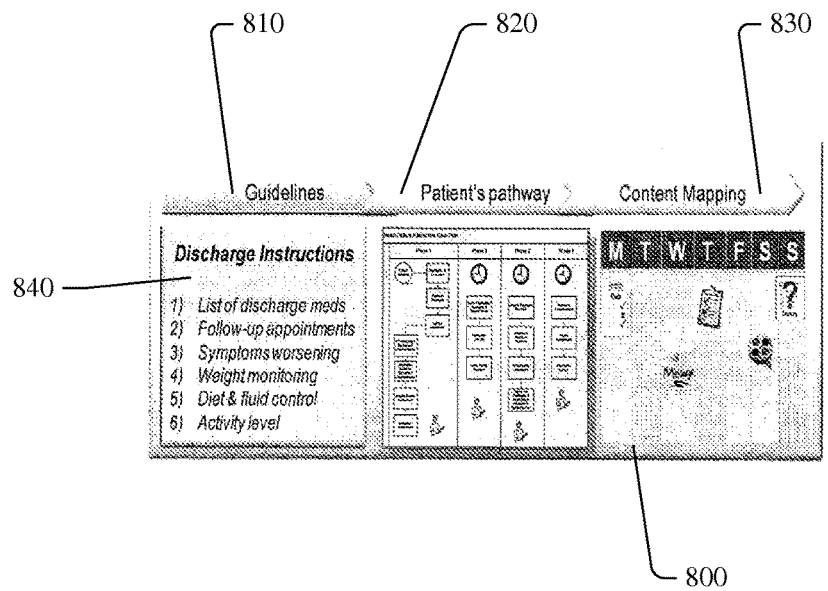

The design of an in-hospital PCP goes through three steps (guidelines, patient's pathway and content mapping) and is illustrated in blocks 810, 820 and 830, respectively of FIG. 8.

Figure 9:
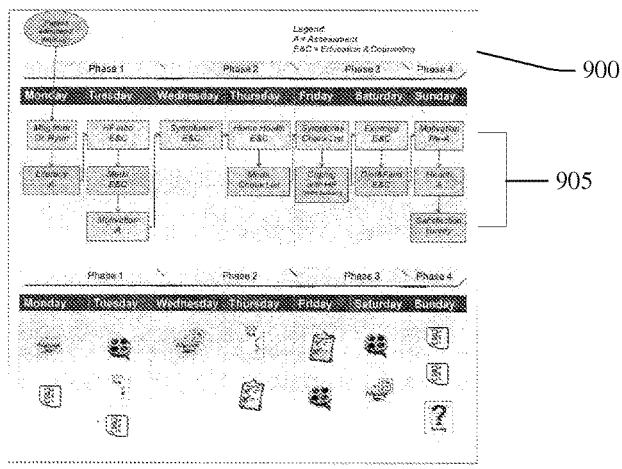

FIG. 9 illustrates a graphical user interface tool 900 which is a zoom out of the patient's pathway illustrated in block 820 of FIG. 8 showing a possible structure of the in-hospital PCP and the content mapping in the PCP in block 830 of FIG. 8.

Figure 10:
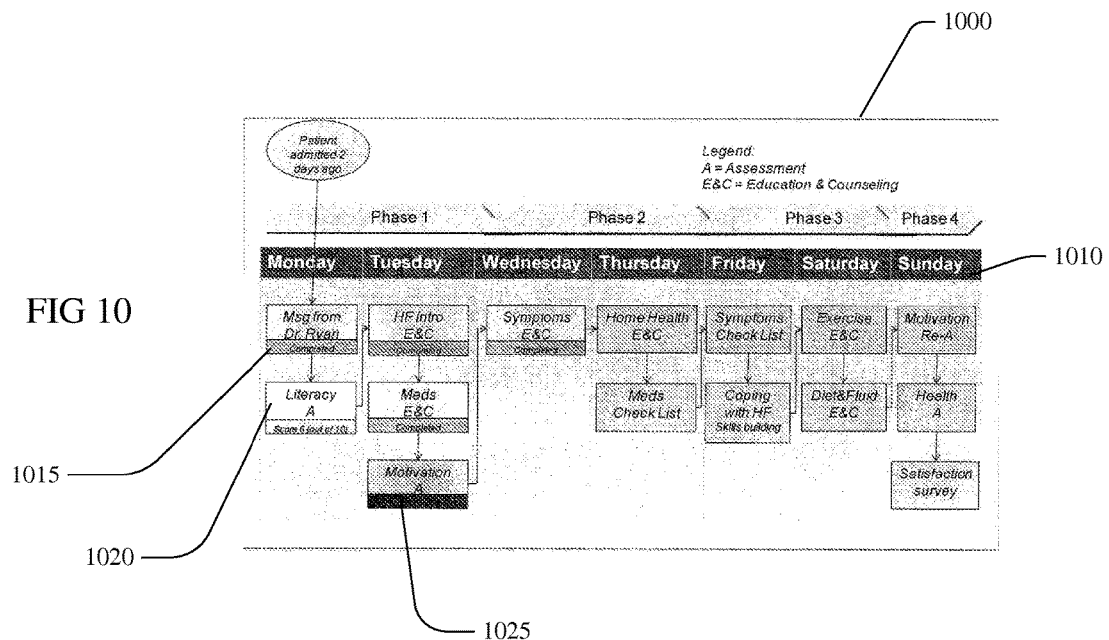

FIG. 10 illustrates a zoom out of a timeline representation of a patient pathway during the PCP of FIG. 9 illustrating an exemplary block 1015 in the pathway which has been completed and an exemplary block 1020 showing the patient's score on an assessment, and an exemplary block 1025 indicative of an alert in case of a low score.

The PCP authoring tools 800, 900 and 1000 will allow clinicians to create and adapt the PCP structure and content, for example, via simple "drag & drop" techniques of structure and content elements, respectively. Such "drag & drop" techniques are known to one of ordinary skill in the art.

In another non-limiting instance, the method 200 employs a timeline representation by day of a patient pathway during the hospital stay. The timeline representation may aid the medical professional in developing the PCP. It is illustrated in FIG. 10, with an indication to the clinician of the current patient's position in the pathway by day (block 1010) in terms of: which blocks have already been completed (for example, see block 1015); a patient's score on an assessment performed (for example, see block 1020); and an alert to a nurse in case of a low score (for example, see block 1025).

With respect to act 250 of FIG. 2, the method 200 generates a summary discharge report 1100 (FIG. 11) with a graphical user interface authoring tool tailored to at least one particular post-discharge care provider from the multidisciplinary care team at the hospital to ensure continuity of care by sharing the HF patient's discharge status. Examples of post-discharge care providers include a primary care physician, an outpatient clinic team, a dietician, a physiotherapist, a pulmonologist, an endocrinologist, the patient, and the patient's family The method 200 invokes a hospital specific template of a structured discharge report 1105 that has at least two sections: a generic section 1110 containing patient's information relevant for all care providers and the patient him/herself, e.g., meds schema, lab results and vitals at point of discharge, appointed care team, etc.; and a tailored section 1120 containing the patient's information relevant for a particular care provider and the patient him/herself, e.g., changes/recommendation in a low sodium diet relevant for a dietician, adaptation in a physical activity relevant for the physiotherapist, adaptation in a number of modules of the out-hospital personalized care plan relevant for the out-patient clinic team, etc.; and the ability to abstract out and modify the education level of the information that is provided to individual providers.

Figure 11:
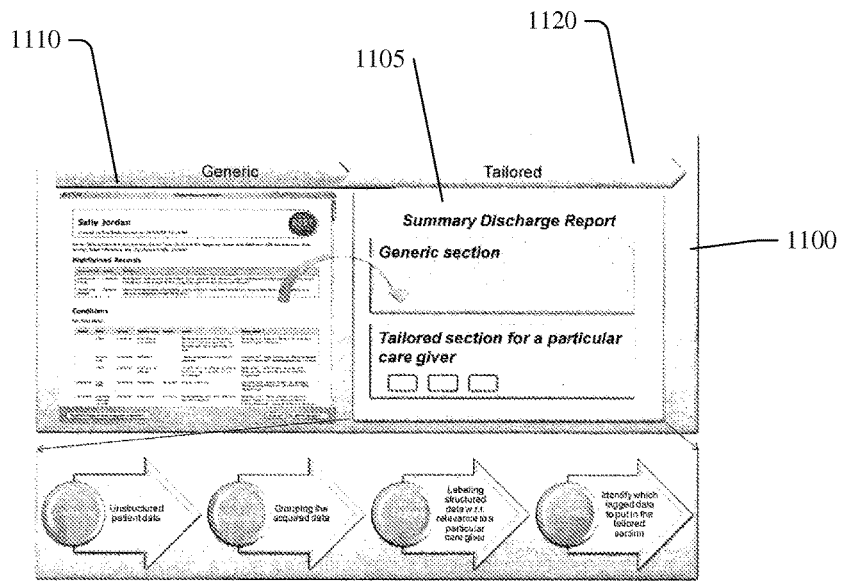

The automatic generation of a tailored section 1120 to a specific care giver using the graphical user interface authoring tool 1100 illustrated in FIG. 11 is the core of this example. It may include the four steps of acquiring, structuring, tagging and selecting patient's data as discussed below.

One aspect of tailoring concerns the roles and responsibilities different care givers have in the post-discharge process, e.g. in some countries, regions or hospitals, the ACEi up-titration process is the responsibility of the cardiologist, while in others a heart failure clinic or even a general practitioner (GP) is responsible, also depending on the severity of HF. In a single region there may be differences depending on the care setting, e.g. if a patient has home care (for HF or another disease) or not. Similarly, a patient with or without social support might need different discharge instructions. In addition, the supporting members need proper instructions.

The summary discharge report 1105 should clearly indicate the roles and responsibilities of the care providers to prevent, e.g. the following situations negatively influencing the total level of care: conflicting and/or confusing messages to the patient, e.g., a cardiologist indicates that for changes in diuretics the patient should consult the GP, while the GP indicates the HF medication can only be changed by the cardiologist; both the GP and cardiologist executing/modifying the up-titration process; and no care provider taking action since each of them thinks another care provider is in charge.

To reach this level of tailoring, the system 100 uses a model that may describe the different care providers, their roles and their responsibilities. This allows the system 100 to be generally applicable, with diversity expressed in the models.

Figure 12:
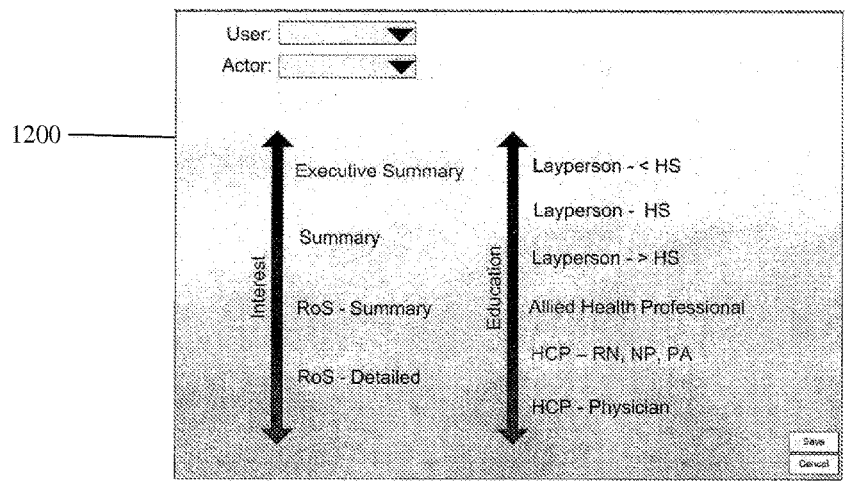

Referring now to FIG. 12, the method 200 includes or invokes a graphical user interface authoring tool 1200 that a user (care provider) may configure different actor profiles and mix the level of interest that they have for a particular role. By combining these two parameters the method 200 may be able to take the single repository of information pertaining to the patient and dynamically construct a presentation of the information for the user reinforcing the idea of the right information, at the right time, in front of the right eyes, in a medium that is actionable by the user.

In addition, the method uses CDS tools for generating an automated discharge summary checklist supporting the medical professionals at the point of discharge. A number of prompts may trigger the care providers to check: a list of discharge medications, and for each medication specified—whether prescribed (Y/N), contraindications (Y/N), and reasons for not prescribing ( . . . ); a list of interventions and counseling performed, and whether for each intervention/counseling performed (Y/N), date performed, notes, etc.; and a list of follow-up services, for each service—scheduled (Y/N), date scheduled, notes, etc.

Figure 13:
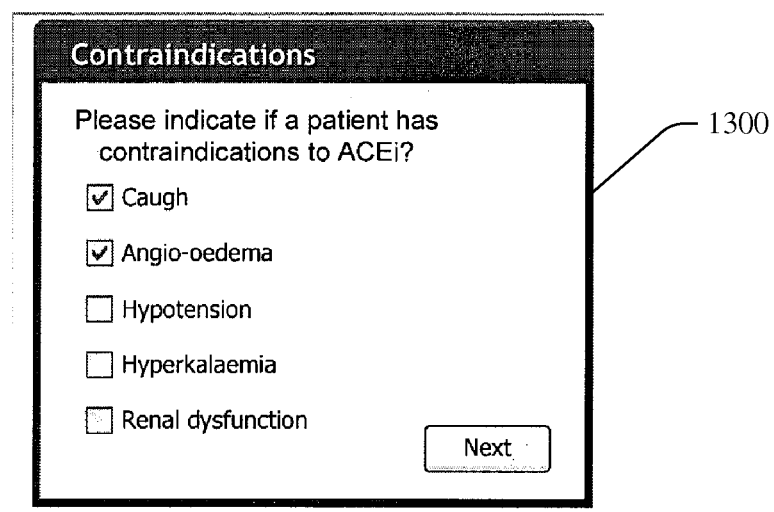

At the point of creating the summary discharge report, a medical professional may be presented with the graphical user interface authoring tool 1300 illustrated in FIG. 13 that provides a "wizard" that would lead the medical professional through the fast and accurate creation of a summary discharge report. (Note that some of these items may be automatically populated by the system from an electronic patient record; in which case the method 200 would only ask via the wizard for the items that are not possible to automatically populate).

For example, a HF patient with LVSD and without ACEi contraindications is not receiving ACEi's which is prescribed by the guidelines and considered standard practice. The medical professional in the out-patient setting needs to know why the patient is not on ACEi's for two reasons: what other medication regime the patient may be on or not restarting the ACEi titration if it was stopped due to angio-oedema, for example (while if the titration was stopped due to patient's choice, adding ACEi's to his medication regime in out-patient setting may be perfectly safe).

An example of a graphical user interface authoring tool or wizard 1300 to aid the medical professional indicate contraindications to ACEi (which will end up on the summary discharge report) is shown in FIG. 13.

Figure 14:
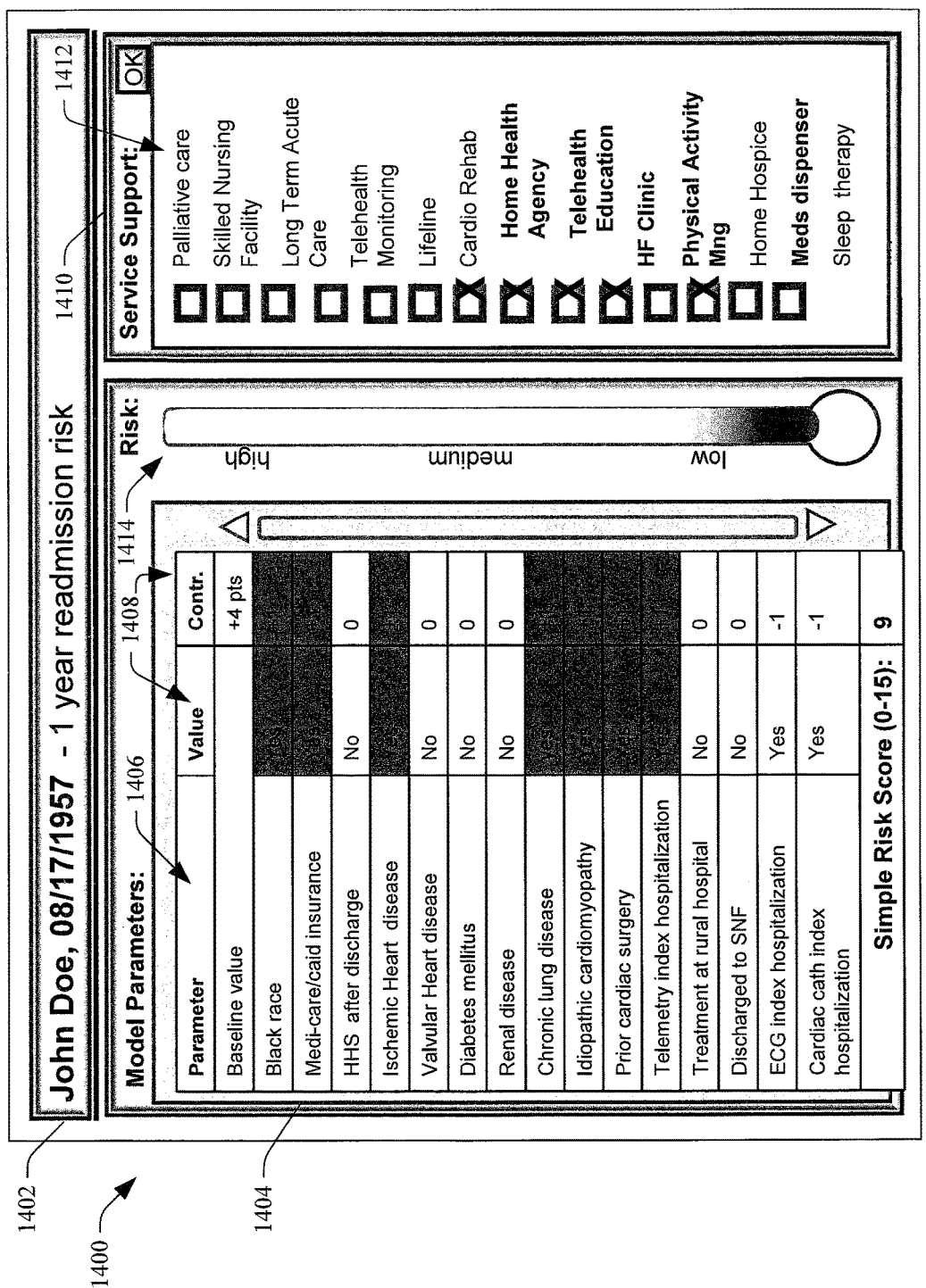

FIG. 14 illustrates a graphical user interface (GUI) 1400 with one or more windows or regions for visually presenting an overview for a patient risk of readmission, e.g., 30 days, 6 months or 1 year post discharge.

In the illustrated example, the patient has been recently hospitalized and identifying his/her risk of readmission is a part of comprehensive discharge planning. A patient identification window or region 1402 presents indicia indicating the patient corresponding to the overview. In the illustrated example, the indicia include the name of the patient and date of birth. The region 1402 may also include other information such as the time frame covered in the planning overview (e.g., "1 year readmission risk") as shown and/or other information. In other example, similar or different information is displayed in the region 1402.

A model parameter window or region 1404 includes a table or list 1406 of risk of readmission parameters. Each parameter is associated with one or more variables 1408. In the illustrated example, each parameter is associated with two variables—value and contribution to the risk (score). In the illustrated example, different visual highlighting is used to distinguish different levels of risk of readmission. As shown, in this example, the visual highlighting is a gray level (e.g., from white to black), with a darker gray level indicating a higher risk and a lighter gray level indicating a lower risk. In a variation of the GUI 1400, the highlighting is additionally or alternatively a color, a font style, a background, a visual effect (e.g., blinking, etc.), etc.

A service support window or region 1410 visually presents a table or list 1412 of available support services, which can be provided to the patient, as selectable and de-selectable graphical icons such as textual icons. An icon and hence the corresponding support service can be selected and de-selected via a mouse, a digital pen, human touch, and/or other known input device. Selecting or de-selecting an icon causes a processor to determine whether the selected or de-selected support service has an impact of the level of risk of readmission for one or more of the parameters 1406. If so, then the processor changes the readmission risk highlighting for the one or more parameters 1406.

By way of example, if providing long term acute care reduces readmission risk associated with chronic lung disease, then selecting "Long Term Acute Care" in the list of services invokes the processor to change the highlighting of the variables corresponding to "Chronic Lung Disease" from a darker shade of gray to a light shade of gray. Subsequently de-selecting the icon will cause the processor to change the highlighting back. An optional risk level indicator 1414 shows the different levels of risk and the corresponding gray levels from low, through medium, to high. In the illustrated example, the highlighting for the parameters includes only high and low risk; however, other levels of gray can be used where the risk is somewhere in between.

It should be noted that the term "including" or "comprising" does not exclude other elements or steps and the "a" or "an" does not exclude a plurality. Also elements described in association with different examples may be combined. It should also be noted that reference signs in the claims shall not be construed as limiting the scope of the claims.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. A method for creating, in electronic format, an actionable care plan for a discharged patient, comprising:
employing via a processor a self-learning algorithm to determine, in real-time, a discharge criteria for a facility by determining: a first percentage of patients discharged while meeting initial discharge criteria; a second percentage of patients not discharged while not meeting the initial discharge criteria, a third percentage of patients discharged while not meeting the initial discharge criteria, and a fourth percentage of patients not discharged while meeting the initial discharge criteria, extending the initial discharge criteria based on the first and second percentages, and deriving additional discharge criteria which reduces the first and third percentages, wherein the discharge criteria for the facility includes the initial criteria and the additional discharge criteria;
determining via the processor that a patient at the facility meets the discharge criteria of the facility;
generating via the processor a numerical value of a risk of re-admission of the patient the facility in response to determining the patient met the discharge criteria;
generating via the processor the actionable care plan, which provides a plan of care for the patient, based at least in part on the numerical value;
constructing via the processor a visual display of the actionable care plan; and
displaying the constructed visual display with a hardware-implemented display monitor.

2. The method of claim 1, wherein the numerical value is a percentage that shows a risk stratification of the patient.

3. The method of claim 1, further comprising:
generating the risk of a re-admission during a predetermined post-discharge period;
generating contributing factors to the risk; and
generating a risk reduction care plan to reduce the risk based on the risk of re-admission during the predetermined post-discharge period and the contributing factors to the risk.

4. The method of claim 1, wherein the self-learning algorithm further determines the discharge criteria based on evidence from patients risk strategy nomograms.

5. The method of claim 1, further comprising:
presenting a representation of the discharge criteria and a patient status with respect to the discharge criteria, including overlaying health parameters, wherein, if the discharge criteria are not satisfied, a list of actions necessary to meet the criteria are provided.

6. The method of claim 1, wherein the discharge criteria includes a condition and a discharge decision, wherein a condition is a Boolean expression evaluated with patient data to check whether a given discharge criterion is satisfied and discharge decision includes an indication that the patient is ready for discharge or not ready for discharge.

7. The method of claim 1, further comprising:
in response to the discharge of the patient where the patient has been classified as not ready to be discharged, reversing the discharge of the patient based on rational applied to multiple patients and that has statistical relevance.

8. The method of claim 1, further comprising:
in response to discharging the patient where the patient has been classified as ready to be discharged, reversing the discharge of the patient based on rational applied to multiple patients and that has statistical relevance.

9. The method of claim 1, further comprising:
presenting the discharge criteria in an interactive graphical user interface in which an authorized user can modify, add, and remove discharge criteria.

10. The method of claim 1, further comprising:
utilizing a discharge criteria domain model and a set of transitions and modelling rules for formalization and customization of discharge criteria.

11. The method of claim 1, further comprising:
collecting and validating a statistically relevant set of discharge criteria via a series of face-to-face meetings and on-line surveys from multiple sites and medical professionals.

12. A system for creating, in electronic format, an actionable care plan for a discharged patient, the system comprising:
a memory that stores instructions; and
a processor that executes the instructions, which cause the processor to:
determine in real time, discharge criteria for a facility by employing a self-learning algorithm that determines a first percentage of patients discharged while meeting initial discharge criteria, determines a second percentage of patients not discharged while not meeting the initial discharge criteria, determines a third percentage of patients not discharged while meeting the initial discharge criteria, determines a fourth percentage of patients discharged while not meeting the initial discharge criteria, and derives additional discharge criteria which reduces the first and third percentages, wherein the discharge criteria for the facility includes the initial and the additional discharge criteria;
determine that a patient meets the discharge criteria for the facility;
generate a numerical value of a risk of re-admission of the patient to the facility in response to the determining the patient met the discharge criteria for the facility;
generate the actionable care plan, which provides a plan of care for the patient, based at least in part on the numerical value;
construct a visual display of the actionable care plan; and
display the constructed visual display with a hardware-implemented display monitor.

13. The system of claim 12, wherein the numerical value is a percentage that shows a risk stratification of the patient.

14. The system of claim 12, wherein the instructions further cause the processor to: generate the risk of a re-admission during a predetermined post-discharge period, contributing factors to the risk, and a risk reduction care plan to reduce the risk based on the risk of re-admission during the predetermined post-discharge period and the contributing factors to the risk.

15. The system of claim 12, wherein the instructions further cause the processor to: employ the self-learning algorithm to identify the discharge criteria based on evidence from patients risk strategy nomograms, which include graphic representation of numerical relationships.

16. The system of claim 12, wherein the instructions further cause the processor to: present a representation of the discharge criteria and a patient status with respect to the discharge criteria, including overlaying health parameters, wherein, if the discharge criteria are not satisfied, a list of actions necessary to meet the criteria are provided.

17. The system of claim 12, wherein the discharge criteria includes a condition and a discharge decision, wherein a condition is a Boolean expression evaluated with patient data to check whether a given discharge criterion is satisfied and discharge decision includes an indication that the patient is ready for discharge or not ready for discharge.

18. The system of claim 12, wherein the instructions further cause the processor to: utilize a discharge criteria domain model and a set of transitions and modelling rules that enable formalization and customization of discharge criteria.

19. The system of claim 12, wherein the instructions further cause the processor to: collect and validate a statistically relevant set of discharge criteria via a series of face-to-face meetings and on-line surveys from multiple sites and medical professionals.

20. A non-transitory computer readable medium encoded with computer executable instructions, which, when executed by a processor of a computer, causes the processor to
- determine, in real time, discharge criteria for a facility by employing a self-learning algorithm that determines a first percentage of patients discharged while meeting initial discharge criteria, determines a second percentage of patients not discharged while not meeting the initial discharge criteria, determines a third percentage of patients not discharged while meeting the initial discharge criteria, determines a fourth percentage of patients discharged while not meeting the initial discharge criteria, and derives additional discharge criteria which reduces the first and third percentages, wherein the discharge criteria for the facility that includes the initial and the additional discharge criteria;
- determine that a patient meets the discharge criteria for the facility;
- generate a numerical value of a risk of re-admission of the patient to the facility in response to the determining the patient met the discharge criteria for the facility;
- generate the actionable care plan, which provides a plan of care for the patient, based at least in part on the numerical value;
- construct a visual display of the actionable care plan; and
- display the constructed visual display with a hardware-implemented display monitor.

* * * * *